(12) United States Patent
Osorio (10) Patent No.: US 11,832,956 B2
(45) Date of Patent: Dec. 5, 2023

(54) SYSTEM AND METHOD FOR OPTIMIZATION IN A PARETO SENSE OF AUTOMATED ABNORMAL BIOLOGICAL EVENT DETECTION AND ABATEMENT

(71) Applicant: Ivan Osorio, Reddick, FL (US)

(72) Inventor: Ivan Osorio, Reddick, FL (US)

( * ) Notice: Subject to any disclaimer, the term of this patent is extended or adjusted under 35 U.S.C. 154(b) by 174 days.

(21) Appl. No.: 17/080,787

(22) Filed: Oct. 26, 2020

(65) Prior Publication Data
US 2021/0145350 A1 May 20, 2021

Related U.S. Application Data

(60) Provisional application No. 62/937,772, filed on Nov. 19, 2019.

(51) Int. Cl.
*A61B 5/00* (2006.01)
(52) U.S. Cl.
CPC ............ *A61B 5/4094* (2013.01); *A61B 5/002* (2013.01); *A61B 5/4836* (2013.01); *A61B 5/746* (2013.01)
(58) Field of Classification Search
CPC .............................. A61B 5/4094; A61B 5/002
USPC .......................................................... 600/300
See application file for complete search history.

(56) References Cited

U.S. PATENT DOCUMENTS

| | | | | |
|---|---|---|---|---|
| 2011/0160795 A1* | 6/2011 | Osorio | ................. | A61B 5/4848 607/45 |
| 2011/0306845 A1* | 12/2011 | Osorio | ................. | A61B 5/7275 600/300 |
| 2012/0083701 A1* | 4/2012 | Osorio | ................. | A61B 5/4094 600/483 |

* cited by examiner

*Primary Examiner* — Nicole F Lavert
(74) *Attorney, Agent, or Firm* — Rodney J. Fuller; BOOTH UDALL FULLER, PLC (57) ABSTRACT

A system and method for finding a Pareto-optimal solution for automated detection, warning, and abatement of a medical condition based on a cost of event intervention in a patient is disclosed. The method includes acquiring at least one biological signal from the patient via at least one sensor of a medical device, detecting an abnormal biological event based on changes in the biological signal, and delivering at least one of a therapy and a warning. The method includes logging a set of parameters including at least one of a detection parameter, a therapy parameter, and a therapy modality. The method includes identifying an optimal set of parameters that yield a Pareto-optimal cost of event intervention by iteratively determining at least one metric over a time window, determining the cost of event intervention, and modifying at least one parameter, until the cost of event intervention meets an acceptability criteria.

20 Claims, 3 Drawing Sheets

SYSTEM AND METHOD FOR OPTIMIZATION IN A PARETO SENSE OF AUTOMATED ABNORMAL BIOLOGICAL EVENT DETECTION AND ABATEMENT

RELATED APPLICATIONS

This application claims the benefit of U.S. provisional patent application 62/937,772, filed Nov. 19, 2019 titled "Event Detection Parameter Optimization as a Function of Costs of Biological Event Detection and Quality of Life," the entirety of the disclosure of which is hereby incorporated by this reference.

TECHNICAL FIELD

Aspects of this document relate generally to the field of automated detection and treatment of medical conditions, and, more particularly, to automated detection and treatment of epileptic events.

BACKGROUND

There have been various advancements in the area of seizure detection, which remains a fairly subjective endeavor. The task of automated detection of epileptic seizures is generally related to and dependent on the definition of what is a seizure, definition which to date is subjective and thus inconsistent within and among experts. The lack of an objective and universal definition complicates not only the task of validation and comparison of detection algorithms, but also (and possibly more importantly), the characterization of the spatio-temporal behavior of seizures and of other dynamical features required to formulate a comprehensive epilepsy theory.

The current state of automated seizure detection is, by extension, a reflection of the power and limitations of visual analysis, upon which it rests. The subjectivity intrinsic to expert visual analysis of seizures and its incompleteness (it cannot adequately quantify or estimate certain signal features, such as power spectrum) confound the objectivity and reproducibility of results of signal processing tools used for automated seizure detection. What is more, several of the factors that enter into the determination of whether or not certain grapho-elements should be classified as a seizure are non-explicit ("gestalt-based") and thus difficult to articulate, formalize and program into algorithms or automated detection systems.

To date, managing non-specificity of changes in extra-cerebral signals such as heart rate for automated, on-line seizure detection and quantification of frequency and severity has been solely based on quantification of the contribution of physiologic factors (e.g., physical activity levels) in the context of the patient's health/physical fitness status and environmental factors (e.g., temperature, humidity, altitude) to increases in heart rate. There is a need to identify methods, means, and devices to optimize parameter selection for automated seizure detection, warning, and delivery of therapy.

SUMMARY

According to one aspect, a method for finding a Pareto-optimal solution for automated detection, warning, and abatement of a medical condition based on a cost of event intervention in a patient includes acquiring at least one biological signal from the patient via at least one sensor of a medical device, the at least one biological signal including at least one of a cardio-vascular signal, a respiratory signal, a dermal signal, an endocrine signal, a metabolic signal, a kinetic signal, and a cerebral signal. The method further includes detecting, via the medical device, an abnormal biological event based on changes in the at least one biological signal, as well as delivering, via the medical device, at least one of a therapy and a warning in response to detection of the abnormal biological event. The method also includes logging to a memory a set of parameters applied as part of detecting, warning, and abating the abnormal biological event, the set of parameters including at least one of a detection parameter, a therapy parameter, and a therapy modality. Lastly the method includes identifying an optimal set of parameters that yield a Pareto-optimal cost of event intervention by iteratively collecting and determining at least one metric over a time window, determining the cost of event intervention based on the at least one metric, and modifying at least one parameter of the set of parameters, until the cost of event intervention meets an acceptability criteria.

Particular embodiments may comprise one or more of the following features. The at least one metric may be selected from the group consisting of: a time elapsed between onset of the abnormal biological event and the delivery of at least one of the treatment and the warning, a false positive detection rate, a false negative detection rate, an efficacy of the therapy, an adverse event rate, an adverse event type, an adverse event severity, and an adverse event timestamp. The at least one metric may include a qualitative assessment of the quality of life of the patient during the time window. Collecting and/or determining the qualitative assessment of the quality of life may include sending an inquiry regarding the quality of life to a mobile device associated with the patient and/or receiving an answer to the inquiry from the patient via the mobile device. The cost of event intervention may meet the acceptability criteria when the cost of event intervention is within an acceptable range. The detection parameter may be at least one of a spectral filter setting, an order statistic filter setting, a detection threshold value beyond which the abnormal biological event is considered detected, and a seizure detection algorithm architecture, and wherein the therapy parameter is at least one of a type of therapy, a dose, a rate of delivery, a current intensity, a current frequency, a current type, a current polarity, a current waveform, a duration of therapy delivery, a timing of delivering therapy with respect to onset of the abnormal biological event, a number of delivery sites, and a delivery site location. The modifying of the at least on parameter may be dictated by one of a receiver operating characteristic curve, a genetic algorithm, and a swarm search. The cost of event intervention may be based on at least one of a cost of detection, a cost of treatment, a cost of injuries, a warning efficiency, an optimization efficiency, an adaptation efficiency, a seizure burden per unit time, an efficacy of electrical stimulation as a function of total electrical energy delivered/unit time, a time spent in detection, a time spent in warning, and a time spent in treatment. The therapy may be at least one of a pharmacologic treatment, a thermal treatment, and an electrical stimulation. The medical device may be one of an implantable device and a portable device outside of the patient. The abnormal biological event may be a seizure, and the medical condition may be at least one of cardiac arrhythmia, fainting, and pain. The acceptability criteria may be defined using one of a receiver operating characteristic curve, a genetic algorithm, and a swarm search.

According to another aspect of the disclosure, a medical device system for finding a Pareto-optimal solution for automated detection, warning, and abatement of a medical condition based on a cost of event intervention in a patient includes at least one sensor, a therapy delivery device, and a medical device having an output device, a processor, and a memory. The medical device is configured to acquire at least one biological signal from a patient using the at least one sensor, the at least one biological signal including at least one of a cardio-vascular signal, a respiratory signal, a dermal signal, an endocrine signal, a metabolic signal, a kinetic signal, and a cerebral signal. The medical device is also configured to detect an abnormal biological event based on changes in the at least one biological signal, and deliver at least one of a therapy using the therapy delivery device and a warning using the output device, in response to detection of the abnormal biological event. The medical device is further configured to log to a memory a set of parameters applied as part of detecting, warning, and abating the abnormal biological event, the set of parameters including at least one of a detection parameter, a therapy parameter, and a therapy modality. Finally, the medical device is configured to identify an optimal set of parameters that yield a Pareto-optimal cost of event intervention by iteratively collecting and determining at least one metric over a time window, determining the cost of event intervention based on the at least one metric, and modifying at least one parameter of the set of parameters, until the cost of event intervention meets an acceptability criteria.

Particular embodiments may comprise one or more of the following features. The medical device may be implantable in the patient. The medical device may be a portable device outside of the patient. The abnormal biological event may be a seizure, and the medical condition may be at least one of cardiac arrhythmia, fainting, and pain. The cost of event intervention may be based on at least one of a cost of detection, a cost of treatment, a cost of injuries, a warning efficiency, an optimization efficiency, an adaptation efficiency, a seizure burden per unit time, an efficacy of electrical stimulation as a function of total electrical energy delivered/unit time, a time spent in detection, a time spent in warning, and a time spent in treatment. The medical device may be communicatively coupled to a mobile device associated with the patient through a network. The at least one metric may include a qualitative assessment of the quality of life of the patient during the time window. Collecting and determining the qualitative assessment of the quality of life may include sending an inquiry regarding the quality of life to the mobile device and/or receiving an answer to the inquiry from the patient via the mobile device. The at least one metric may be selected from the group consisting of: a time elapsed between onset of the abnormal biological event and the delivery of at least one of the treatment and the warning, a false positive detection rate, a false negative detection rate, an efficacy of the therapy, an adverse event rate, an adverse event type, an adverse event severity, and an adverse event timestamp. The detection parameter may be at least one of a spectral filter setting, an order statistic filter setting, a detection threshold value beyond which the abnormal biological event is considered detected, and a seizure detection algorithm architecture, and wherein the therapy parameter is at least one of a type of therapy, a dose, a rate of delivery, a current intensity, a current frequency, a current type, a current polarity, a current waveform, a duration of therapy delivery, a timing of delivering therapy with respect to onset of the abnormal biological event, a number of delivery sites, and a delivery site location. The modifying of the at least one parameter may be dictated by one of a receiver operating characteristic curve, a genetic algorithm, and a swarm search.

Aspects and applications of the disclosure presented here are described below in the drawings and detailed description. Unless specifically noted, it is intended that the words and phrases in the specification and the claims be given their plain, ordinary, and accustomed meaning to those of ordinary skill in the applicable arts. The inventors are fully aware that they can be their own lexicographers if desired. The inventors expressly elect, as their own lexicographers, to use only the plain and ordinary meaning of terms in the specification and claims unless they clearly state otherwise and then further, expressly set forth the "special" definition of that term and explain how it differs from the plain and ordinary meaning. Absent such clear statements of intent to apply a "special" definition, it is the inventors' intent and desire that the simple, plain and ordinary meaning to the terms be applied to the interpretation of the specification and claims.

The inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors are fully informed of the standards and application of the special provisions of 35 U.S.C. § 112(f). Thus, the use of the words "function," "means" or "step" in the Detailed Description or Description of the Drawings or claims is not intended to somehow indicate a desire to invoke the special provisions of 35 U.S.C. § 112(f), to define the invention. To the contrary, if the provisions of 35 U.S.C. § 112(f) are sought to be invoked to define the inventions, the claims will specifically and expressly state the exact phrases "means for" or "step for", and will also recite the word "function" (i.e., will state "means for performing the function of [insert function]"), without also reciting in such phrases any structure, material or act in support of the function. Thus, even when the claims recite a "means for performing the function of . . . " or "step for performing the function of . . . ," if the claims also recite any structure, material or acts in support of that means or step, or that perform the recited function, then it is the clear intention of the inventors not to invoke the provisions of 35 U.S.C. § 112(f). Moreover, even if the provisions of 35 U.S.C. § 112(f) are invoked to define the claimed aspects, it is intended that these aspects not be limited only to the specific structure, material or acts that are described in the preferred embodiments, but in addition, include any and all structures, materials or acts that perform the claimed function as described in alternative embodiments or forms of the disclosure, or that are well known present or later-developed, equivalent structures, material or acts for performing the claimed function.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

The disclosure will hereinafter be described in conjunction with the appended drawings, where like designations denote like elements, and.

DETAILED DESCRIPTION

This disclosure, its aspects and implementations, are not limited to the specific material types, components, methods, or other examples disclosed herein. Many additional material types, components, methods, and procedures known in the art are contemplated for use with particular implementations from this disclosure. Accordingly, for example, although particular implementations are disclosed, such implementations and implementing components may comprise any components, models, types, materials, versions, quantities, and/or the like as is known in the art for such systems and implementing components, consistent with the intended operation.

The word "exemplary," "example," or various forms thereof are used herein to mean serving as an example, instance, or illustration. Any aspect or design described herein as "exemplary" or as an "example" is not necessarily to be construed as preferred or advantageous over other aspects or designs. Furthermore, examples are provided solely for purposes of clarity and understanding and are not meant to limit or restrict the disclosed subject matter or relevant portions of this disclosure in any manner. It is to be appreciated that a myriad of additional or alternate examples of varying scope could have been presented but have been omitted for purposes of brevity.

While this disclosure includes a number of embodiments in many different forms, there is shown in the drawings and will herein be described in detail particular embodiments with the understanding that the present disclosure is to be considered as an exemplification of the principles of the disclosed methods and systems, and is not intended to limit the broad aspect of the disclosed concepts to the embodiments illustrated.

The use of biological signals (e.g., electrical, acoustic, chemical) for the automated detection, quantification, and abatement of abnormal biological events (e.g. seizures, etc.), generated by organs (e.g., heart, lungs, etc.) whose function is modulated by the brain but whose signals are not recorded from the scalp or intra-cranially (hereinafter referred to as extra-brain signals), offers multiple advantages over the use of signals generated by the brain and recorded from the scalp or intracranially (hereinafter referred to as brain signals). Using extra-brain signals is markedly less costly (and more cost-effective) for clinical applications. Their use is much easier and quicker to implement for commercialization.; Extra-brain signals are easier to record and more robust (e.g. higher signal to noise ratio, etc.) than those generated by the brain and are also simpler to process and analyze, all valuable properties for real-time detection with battery-powered devices (especially if implantable). Additionally, there are thousands of surgeons in the United States capable of implanting detection, warning and therapy delivery devices anywhere in the body (but in the head/brain), compared to a few hundred functional neurosurgeons with training for intracranial device implantation.

There is, however, an important limitation in the use of extra-brain signals for automated seizure detection compared to those generated by the brain, namely a lack of specificity. For example, increases in heart or respiratory rate occur upon arousal from sleep, upon sitting or standing up from a recumbent position, while performing a physical activity or experiencing emotions (e.g., excitement, fear, anger, etc.). Motor activity/movement, widely used medications with effects on the central and peripheral autonomic (sympathetic and parasympathetic) nervous system and the cyclic changes in environmental conditions (e.g., ambient temperature, humidity, etc.) are likely to confound seizure detection based on cardio-vascular (e.g., heart rate and/or rhythm, blood pressure, stroke volume), respiratory (e.g., frequency or rate, tidal volume, pattern, blood oxygen saturation) or electro-dermal (e.g., skin resistance, temperature, perspiration) signals.

Managing non-specificity of the detection of abnormal biological events such as seizures using, for example, cardiac signals (e.g., heart rate) can be accomplished by quantifying the contribution of physiologic factors (e.g., physical activity levels) in the context of the patients' health/physical fitness status and environmental factors (e.g., temperature, humidity, altitude), and in that context, finding an optimal set of parameters for the detection, warning, and abatement of the abnormal biological event.

Contemplated herein is a system and method for finding a Pareto-optimal solution for the automated detection, warning, and abatement of abnormal biological events caused by a medical condition (e.g. cardiac arrhythmia, fainting, pain, etc.). This system and method yields an optimal set of parameters (or multiple optimal sets of parameters) for the detection, warning, and abatement of the medical condition. These sets of parameters are is Pareto-optimal in the context of a Cost of Event Intervention (hereinafter CoEI) in the patient.

In the context of the present description and the claims that follow, a "cost", such as the CoEI, is a measure of the impacts, both positive and negative, a set of parameters has on various aspects of the effort to detect, warn, and abate the events associated with the medical condition. According to various embodiments, these costs are metrics that are used by the system and method contemplated herein to arrive at a set of parameters that result in a desirable outcome. Costs and other metrics will be discussed in much greater detail, below.

The system and method contemplated herein finds a Pareto-optimal solution for the automated detection, waring, and abatement of abnormal biological events, or pathological state changes in patients with medical conditions such as epileptic seizures, cardiac arrythmias, fainting, pain, or the like. These solutions are optimized, in a Pareto sense, for the performance of any or all of the tasks of detecting the onset of an abnormal biological event, warning the patient and/or medical caregiver of said event, and/or providing treatment for the abatement of said event. As will be discussed further, below, it is rarely possible to simultaneously and collectively improve all of the factors and parameters for these outcomes. Additionally, the needs and circumstances of patients vary wildly; what may be an ideal solution for one patient may be disastrous for another, even if they both suffer from the same medical condition. The system and method contemplated herein makes it possible to arrive at an ideal or near ideal outcome that takes into account the specific circumstances of each patient, in less time and with less experimentation than what is needed using conventional methods.

Costs, such as the CoEI, may have monetary and clinical aspects. The clinical component encompasses potential complications associated with the: a) surgeries required to implant electrodes/sensors and devices for recording, processing and analyses of biological signals, for the performance of automated detection, warning, logging and treatment or prevention of pathological state changes; b) failure to gain the maximum desirable benefit due to the competing nature of the objectives as many of the observables of the automated event detection task such as sensitivity and specificity co-vary negatively, meaning that as one is improved the other is inexorably degraded. The negative co-variance of sensitivity and specificity impact, in turn, the speed of automated detection, warning times and timing of warnings, patient safety, patient comfort and therapeutic efficacy, as will be discussed below; c) Direct effects on health status and quality of life of the degree of complexity and of the time required to find the optimal, in a Pareto-sense, therapeutic modality (e.g., electrical, chemical, thermal or cognitive) and therapeutic parameters (e.g., current intensity or frequency, drug type or dose, tissue cooling or heating and temperature settings, etc.).

Optimization of event detection parameters and the functions it enables (e.g., warnings, therapy delivery, etc.) is in many patients a multi-objective optimization. In reality, the number of objectives (e.g., specificity, efficacy of therapy, number and timing of warnings, etc.) subject to optimization is likely to vary within (intra-) and between (inter-) patients, with environmental conditions (e.g., temperature, etc.) and with circadian and ultradian rhythms. In the context of competing objectives (e.g., specificity of seizure detection vs. sensitivity of seizure detection vs. therapeutic efficacy, vs. patient safety), optimization as contemplated herein does not mean that there is a single optimal solution, but rather there is often a set of alternative solutions. These solutions are optimal in the sense that no other solutions in the search space are superior to them when all objectives are considered. These are known as Pareto-optimal solutions. In some embodiments and implementations, this optimization problem is linear, while in others it may be non-linear. Methods and techniques that are suitable for both will be applied. Regarding the matter of constraint (constrained vs. un-constrained optimization), clinical applicability is likely to benefit more from constrained than from un-constrained optimization, but both may be applied as needed, according to various embodiments.

State-of-the-art automated seizure detection using extra-brain signals (e.g., metabolic, endocrine, respiratory, movement/kinetic, dermal, cardio-vascular etc.) will be advanced by applying the methods, systems and devices contemplated herein. It is worth noting that the concept of Cost of Event Intervention (to be discussed in more detail below), is generalizable to any form of automated event detection, warning and treatment independent of the signal used, the therapy target, the therapeutic modality or the disorder/disease under consideration.

According to various embodiments, a medical device system configured with sensors and therapies for application to a patient is given a set of parameters that define how the device examines the biological signals gathered from a patient by the sensors, in order to detect the onset of an abnormal biological event. The medical device acquires at least one biological signal from the patient. Based on changes in these signals, the medical device detects an abnormal biological event. In response to detecting this event, the medical device may provide a warning to the patient or other interested party and/or automatically administer a therapy to reduce the severity and/or length of the event. Each event detected by the medical device is logged; specifically, the parameters that were in use at the time of detection, as well as data describing the event itself. These parameters and metrics are collected over a time window. At the end of the time window, the collected metrics (and metrics derived from collected data) are used to determine the CoEI, thus assigning a value to the medical device's performance of its duties during that time window. If the CoEI meets an acceptability criteria, that set of parameters is deemed to be a Pareto-optimal solution and are continued to be applied in the monitoring and treatment of the patient. If the acceptability criteria have not been met, the CoEI is used as a basis for modifying at least one of the parameters that was in use. According to various embodiments, that modification is made in accordance with an optimization strategy, as will be discussed below. This continues until arriving at a CoEI that meets the acceptability criteria, or the optimization process is halted by an individual (e.g. patient, doctor, etc.).

As mentioned above, the system and method contemplated herein detects abnormal biological events such as seizures, and further optimizes, in a Pareto sense, parameters associated with the detection, warning, and abatement of said events, using biological signals obtained by a medical device having one or more sensors observing the patient. Exemplary signals include, but are not limited to, a cardio-vascular signal, a respiratory signal, a dermal signal, an endocrine signal, a metabolic signal, a kinetic signal, a cerebral signal, and the like. Those skilled in the art will recognize that these signals may be obtained using various sensors known in the art. The most appropriate sensor for a particular embodiment or even a specific patient may depend on the context of the treatment, as well as the condition of the patient (e.g. ambulatory vs confined to bed, etc.).

In some embodiments, all of the biological signals considered by the system may be gathered directly by the contemplated medical device. In other embodiments, the medical device may gather some information directly, while other information may be obtained from external systems employing their own sensors. For example, some biological signals may be easier to obtain from systems already in use. Additionally, patient comfort may be enhanced by minimizing the number of redundant sensors applied to their body.

Some embodiments of the medical device may be configured to cooperate with external devices in communication with the medical device, whether for the purpose of sharing data or off-loading the processing involved in applying certain optimization methods. The algorithms and strategies for parameter optimization require adaptation through learning, which in turn requires the acquisition, processing and analyses of large data sets under real-life conditions and situations for each patient. In some embodiments, additional devices may be employed to accomplish this, as will be discussed further with respect to FIG. 1, below.

The system and method for finding a Pareto-optimal set of parameters for the medical device examines the cost of event intervention (CoEI), and the effects that modifying one or more of the parameters has on it. Again, in the context of the present description and the claims that follow, the word "cost" is not being limited to an expense or a loss, monetary or otherwise, but is instead used to convey the value rendered by a set of parameters. That value is conveyed such that the values of two sets of parameters may be easily compared with each other.

According to various embodiments, the CoEI and the other "Costs" discussed below are metrics. Some of these costs, including the CoEI, are derived from other metrics which may be directly observed, either by an individual and entered into the memory of the medical device, or observed through the one or more sensors communicatively coupled to the medical device.

There is no strict definition for how the CoEI is derived. Because the needs of each patient can vary widely, the CoEI may be defined on a case by case basis. For example, an individual who is often driving a car would have a CoEI that placed greater value on the reduction of the severity of abnormal biological events which could result in loss of consciousness or motor control leading to a potentially fatal car accident, even if such a parameter set would lead to an increase in the number of events. Another patient who is homebound may be best served by a different CoEI.

According to various embodiments, the Costs of Event Intervention (CoEI) may comprise the Cost of Detection, the Cost of Treatment, the Cost of Injury, and/or a Quality of Life Cost. These costs may be calculated or estimated collectively or separately, given that the clinical value/usefulness of these four applications is under the control of automated detection, according to various embodiments. For example, in one embodiment, parameter selection for automated event may be dictated by the cost/expense (negative impact) inherent to the search for optimal (in a Pareto sense) sensitivity (measured as the rate of false negative detections) and allowable specificity (measured as the rate of false positive detections) and their effect on the speed of event detection, the number and efficacy of warnings, patient safety, and therapeutic efficacy that collectively constitute an optimal solution in a Pareto sense, for that particular patient.

Since adverse side effects may be associated with certain treatment modalities or with certain treatment parameters, if present, they will negatively impact CoEI. In general, the higher the therapeutic efficacy and the lower the rate of adverse effects and their severity, the lower the CoEI and the more suitable the Pareto-optimal solution.

Below are examples of Costs and other metrics (listed in no particular order) that may be used to evaluate and compare different sets of parameters in the search for a Pareto optimum for a particular patient. It should be noted that these costs/metrics do not encompass the entirety of available options and of possible permutations. Additionally, there may be some overlap between entries, particularly with respect to the costs, which may have interest in the same metrics to achieve different goals, according to various embodiments.

Cost of Detection

Pathological events such as seizures carry a risk of injury (potentially fatal) due to falls to the ground, burns, vehicular accidents, cardiac arrythmias, and the like, underscoring the importance of timely delivery of treatment and issuance of warnings to prevent or lessen the impact of a negative outcome. The term "timely" means that to be effective, the treatment or warning must be delivered at the onset of the abnormal biological event, or shortly (e.g., up to 5 sec) after its onset. The context of the present description and the claims that follow, the term "onset" corresponds to the first manifestation (e.g., a change in a biological signal, whether or not associated with a clinical correlate) indicative of the transition into the pathological event.

Thus, timely delivery of a therapy or issuance of a warning are critically dependent on the speed with which the event is detected. In some embodiments, the speed of automated seizure detection (SSzD) is the time elapsed between the earliest change (i.e., onset) in a patient's biological signals (e.g., brain, cardio-vascular, autonomic, etc.) caused by paroxysmal (e.g., seizure) activity and the issuance of a detection based on changes on said biological signals. Likewise, according to various embodiments, speed of seizure treatment (SSzT) is the time elapsed between the issuance of a detection and an automated action (e.g. delivery of therapy) in response to said detection.

According to various embodiments, Speed of seizure detection determines therapeutic efficacy and patient safety, since the faster the SSzD, the sooner therapies may be delivered, and warnings issued. In general, the higher the SSzD, the higher the probability of automated abatement (i.e., higher efficacy) and in all cases, the longer the window to implement safety measures and the higher the probability of preventing injuries. The cost of high SSzD, the by-product of high detection sensitivity, is an increase in the rate of false positive detections, warnings, unnecessary treatments, increased exposure to potential adverse therapy and other effects plus unwarranted reduction in battery life. The cost of enhanced specificity of detection, a by-product of slower SSzD, is decreased therapeutic efficacy and increased risk of injury.

Speed of seizure detection (SSzD) is a highly important performance feature of any detection algorithm, and it co-varies negatively with adjustments (improvements or deteriorations) in specificity and directly with changes in sensitivity. Changes in SSzD in turn, impact positively or negatively on crucial objectives such as efficacy of warnings (to maximize patient safety) and therapies when these are added to automated seizure detection. Improvements in specificity of detection cause delays in issuance (relative to lower specificity) of detections, negatively impacting (i.e., delaying) therapy delivery and implementation of safety measures before a patient's awareness or consciousness becomes impaired.

Simply defined, the Cost of Detection (COD) is the "trade-off" inherent in the selection of competing detection parameters that predictably improves one detection performance metric (e.g., specificity) at the expense of another (e.g., sensitivity) or vice-versa. In other words, since concurrent/parallel/simultaneous optimization of two or more detection metrics (specificity and sensitivity) is not possible, there is a cost to improving one, which is estimated or measured as the magnitude in the decline or worsening of the other. For example, parameters that optimize sensitivity of detection typically degrade specificity with the inevitable (but manageable) increase in false detection rates (a negative outcome) and SSzD (a positive outcome). Improvements in specificity reduce false positive detection rates and potential adverse effects (positive outcome), but impair sensitivity and SSzD, delaying delivery of therapy and shortening the window within which safety measures may be adopted (negative outcome). The cost of detection is thus, the net gain or loss inherent to the "tradeoff" in upgrades (or downgrades) in specificity or sensitivity, relative the ideal case (i.e., no trade-off).

Quantitative assessments of COD may be expressed as numerical indices that are compared to the ideal performance or outcome value. The following are non-limiting examples for COD: Ideal detection algorithm performance is 0 false positives (FP) per unit time and 0 false negatives (FN) per unit time and in another embodiment, deviations from it (e.g., 1 FP/hour) may be expressed as an algebraic sum [Expected false positive detection rate: 0—Observed: 1 (0−1=−1); Expected false negative detection rate: 0—Observed: 2.3 (0−2.3=−2.3) and this is the COD index; the higher the negative number for FPs and FNs, the higher the COD (i.e., the poorer the performance).

Improved specificity of seizure detection can be achieved by obtaining a biologically representative sample from a patient endowed with an intelligent/automated seizure detection, warning and treatment device. Biologically representative samples as understood herein, are those that accurately reflect the status of the organ or organism, varying with the status of the patient and with environmental conditions. In some embodiments, this representativeness may mean statistical significance as defined conventionally, while in other embodiments representativeness may mean something else. It is anticipated that the size of what constitute a biologically representative sample will vary among patients, and as a function of COD or CoEI.

Quality of Life Cost

Quality of Life Cost (QLC) depends on the efficacy of the therapy and of the warnings, the rate and number and severity of adverse effects including the distress/anxiety caused by excessive false positive detections or by seizure detection failures (false negative). According to various embodiments, the assessment of the QLC may be qualitative or quantitative.

Qualitative assessment of QLC is subjective (patient or caregiver). In some embodiments, the ratings may be binary (e.g., ACCEPTABLE or UNACCEPTABLE) while in others they may have more granularity (e.g., POOR, FAIR, GOOD, EXCELLENT). For example, in one embodiment, a question (e.g. "(Is the most recent change to your detection algorithm acceptable?", etc.) will automatically appear on the screen of a cell phone or some other mobile device communicatively coupled to the medical device. The inquiry is sent sometime (e.g. 24 hours, 96 hours, etc.) after a change in a detection parameter. As a specific example, a spectral filter or a wavelet with a broad power spectrum (e.g., 8-42 Hz) is replaced by one with a narrower power spectrum (15-35 Hz.). The options YES or NO are shown on the screen and the patient may manually or orally choose one. If the answer is YES, a follow up question (e.g. "How would you grade the change?" with options such as FAIR? GOOD? EXCELENT?) pop up on the screen for the patient to choose. If the answer to the question "Is the most recent change to your detection algorithm acceptable?" is NO, the current detection parameters may be automatically replaced by previously acceptable (to the patient or caregiver) parameters, and the data collected under the unacceptable parameters related to seizures/unit time, seizure severity, inter-seizure interval, number of false positive (or negative) detections and time of day or month when seizures occurred, type of activities the patient was involved in (e.g., sitting down vs. operating a vehicle) when seizures occurred, number/unit time, type and severity of adverse effects collected since the time the parameters were changed, may be analyzed (on- or off-line) and compared to data saved to memory under the previous acceptable or safe detection parameter, to determine and characterize the differences between them. Since subjective assessments are prone to inaccuracies, if the quantitative analyses show that the change in the detection parameter led to a Pareto-optimal solution, the parameters the patient deemed UNACCEPTABLE may be automatically reinstituted.

In some embodiments, the determination of the Quality of Life Cost may be quantitative. The greater the improvement in quality of life, the more suitable the Pareto-optimal solution and the lower the CoEI. Validated instruments such as the Quality of Life Scale, McGill quality of life questionnaire Health-related quality of life WHOQOL-BREF, and quality of life in Epilepsy-31 among many others may be also used.

Cost of Treatment

According to various embodiments, the Cost of Treatment (COT) may be calculated by comparing the severity of treated vs. untreated seizures. Seizure severity (SzS) in one embodiment, may be estimated for example, as the product of the maximal heart rate (HR), and the time (in sec.) the heart rate remains above non-seizure heart rates (SzS=HRmax×time spent in HR above non-seizure heart rates). The mean or median seizure increase in HR may be used instead of HRmax; let's say, the median maximal HR in a sample of un-treated seizures is 125 bpm and median duration of HR above a non-seizure reference value is 52 sec and the severity of a sample of treated seizures (using a set of identical parameters as those for detection of the un-treated seizures) is 98 bpm and duration of HR above a non-seizure reference value is 29 sec: COT=Un-treated SzS=125×52=6500—Treated SzS=98×29=2842 or −44% if expressed as percentage reduction, in which case COT is 66% [COT=(desirable SzS reduction: 100%—observed SzS reduction: −44%). The lower the COT, the more efficacious the therapy. Since treatments may intensify events, increases in severity may be expressed as percentage changes (e.g., +160% or +1.6). This example is based on seizure detection using heart rate, but it is generalizable to detection using cerebral (e.g., cortical or sub cortical electrical or other signals (see Osorio references below).

In some embodiments, the COT may be also expressed as the product of percentage change in seizure frequency (i.e. increases are identified by the positive symbol (+) and decreases by the negative (−)) and in seizure severity (i.e. intensity×duration) or using any informative mathematical expression (arithmetical, algebraic, etc.) (e.g., % change seizure frequency×% change intensity×% change duration; 1/change in seizure frequency+1/change in seizure intensity+1/seizure/change in seizure duration, etc.). Seizure severity and/or frequency may be also conveyed in percentile values. For example, the mean or median severity or frequency of seizures prior to treatment may correspond to the 100 th percentile against which decreases or increases are computed.

As a specific example of a Pareto-optimal solution in automated seizure detection and treatment, an anti-seizure treatment may increase the number of seizures/unit time while markedly reducing their severity. After automated delivery of a certain therapy was sped up by 4 sec., a patient who had 1 convulsion or generalized tonic-clonic seizure/day (invariably associated with loss of consciousness and fall to the ground), began having 5 partial simple seizures/day during which the patient remained fully functional, a marked improvement (due to reduction in severity), notwithstanding the marked increase in daily frequency. A conventional approach to assessment of therapeutic efficacy may have yielded, in this case, erroneous results if only seizure frequency (estimated based on patient diaries), traditionally the golden metric for state-of-the art therapy assessment, would have been applied.

The multi-objective or multi-dimensional approach contemplated herein (taking into account severity, not just frequency), may have deemed this clinical result as a Pareto-optimal solution. For the sake of simplicity, only frequency and severity are used as example of a multi-objective approach to the optimization of automated seizure detection. The extent of seizure spread, inter-seizure interval, the number of false positive (or negative) detections, the time of day or month when seizures occur, the type of activities the patient was involved in (e.g., sitting down vs. operating a vehicle) when a seizure occurred and number, the type and severity of adverse effects would be included in the optimization process as needed, to improve a patient's condition and quality of life, according to various embodiments. Reduction in seizure frequency by a therapy may also result in increases in their severity.

Cost of therapy may be also assessed based on an efficacy of the therapy, and/or the efficiency of a therapy. According to various embodiments, therapeutic efficacy may be quantified as the decrease in the number of seizures/unit time and of their severity.

According to various embodiments, efficiency (€) may have more than one definition or meaning. In some embodiments, € is the ratio of the number (n) of treatments/unit time (t) (e.g., 24 hrs.) that reduced SzS or frequency by a certain quantity q, divided by the total number (N) of stimulations per t [nt decreasing SzS or frequency q/Nt].

As a specific, non-limiting example, in 24 hrs.: i) 15 treatments (e.g., electrical stimulations or drug infusions) were delivered in response to 15 valid automated event detections; ii) every stimulation reduced the event's severity and iii) mean severity was reduced by 70%, then, €=15× 0.7/15=0.7. In a different patient, the same number of treatment (15) were administered over 24 hrs., but severity was reduced only in 8 events by a mean of 80%, then €=10×0.8/15=0.5. To gain more insight into treatment €, the number of attempts/event that yield for a satisfactory (e.g. abatement or blockage of pathological events) outcome and it is applicable to any therapeutic modality; €=1/Total number of Treatments×Reduction in Severity. By way of example, if 3 electrical stimulation or 3 drug deliveries are required to lessen the severity on an event and the reduction is by 50%, then, €=⅓×0.5=0.16. The higher the ratio value, the more efficient the therapy with 1 being the maximum possible value. Treatment efficiency may be also calculated as sole function of event frequency or of change in severity.

Treatment Efficiency allows for the indirect assessment of sensitivity of event detection as treatment of FP detections will reduce €. Continuing a previous non-limiting example from above, in 24 hrs.: i) 15 treatments (e.g., electrical stimulations or drug infusions) were delivered in response to 8 valid automated event detections (7 FPs); ii) every stimulation reduced the event's severity and iii) mean severity was reduced by 70%; €=True Detections/Total Number of Detections×SSz change/Total Number of Treatments=10/15×0.7/15=0.03

Cost of Injury

According to various embodiments, the cost of injury (COI) may be based on the number, type, severity, and/or temporal spacing of adverse events. Three classes of adverse events may be considered: i) those caused by therapies (e.g., pharmacologic, electrical, thermal, etc.) either idiosyncratic or dose-dependent (e.g., overtreatment), the latter being more likely the higher the false positive detection rate; ii) those caused by insufficient time to implement safety measures that result in injury regardless of severity and length of incapacity; iii) those caused by excessive warnings whether or not corresponding to false positive detections. Warnings cause anticipatory fear/anxiety in patients; in this case, reduction in the number of superfluous warnings would bring relief to patients and those around them. Adverse effects negatively impact Quality of Life (QOL) and may impair it to a greater degree than the actual pathological state changes (e.g., epileptic seizures).

The shorter the latency (a result of faster SSzD) between the emergence of the first change in a biological signal indicative of an abnormal biological event and the issuance of a detection, the higher the false positive detection rate, number of false warnings and unnecessary treatments but the lower the risk of injury and of treatment failure. Furthermore, while the longer the latency (a result of slower SSzD) between the emergence of the first change in a biological signal indicative of a seizure and the issuance of a detection, the lower the false positive detection rate and number of false warnings and unnecessary treatments, but the higher the risk of injuries and failure of treatment. The inter-play between sensitivity and specificity of detection and its adverse impact on patient safety and therapeutic efficacy, illustrated above, explain why their co-variance is negative.

Since specificity and sensitivity are competing objectives, that is, upgrading one inevitably degrades the other, it is required when clinically indicated in some embodiments, to prioritize (rationally and quantifiably) sensitivity over specificity or vice-versa for each subject according to: i) the degree/level of safety risks associated with patient activities (e.g. operating a vehicle vs. sitting on a chair at home, etc.); ii) the rate of diffusion of a therapeutic agent or time required by a therapeutic agent to reach and diffuse throughout the epileptogenic zone; iii) the inherent efficacy of a therapy (high vs. low); iv) therapy adverse effects; v) excessive warnings which negatively impact quality of life, and vi) impact on battery life and risks and cost of battery replacement In some embodiments, the COI is correlated with the time available, between warning issuances and loss of awareness or of consciousness, to implement safety measures and/or deliver a therapy. It is worth pointing out that highly efficacious therapies with rapid onset of action may lessen reliance upon warnings, and that the availability of long windows to implement safety measures mitigates, in part, the lack of therapeutic efficacy. As a specific non-limiting example, a patient with a mean of 5 seizures/week (3 complex partial and 2 secondarily generalized (convulsions)) suffered 2 injuries/month (0.5/week) which is the COI for this patient. When detection parameters S2 were introduced, injuries ceased occurring (COI=0), even though the patient still had 1 seizure/week; this was the result of increasing speed of detection (parameter set S4 sped up detection by 5.3 sec. compared to 51), thus prolonging the time between the issuance of the warning and the loss of consciousness and allowing implementation of safety measures.

In addition to quantifying an adverse event rate, adverse events may be quantified by their type (e.g., burns, trauma), the severity of injuries (e.g., 2nd vs. 3rd degree burns; comminuted vs. non-comminuted fractures; brain contusion vs. brain laceration) or extent (e.g., 20% vs. 50% body surface burns; radial vs. hip fracture; 3.9 cc. brain hematoma vs. 11 cc. brain hematoma) and/or duration and degree of disability they cause or by the time required for the patient to fully or partially recovery (which can be derived from an adverse event timestamp recorded to memory by the medical device). In some embodiments, a value on a linear, exponential or logarithmic scale may be assigned to injuries. For example, 1st degree burns may be assigned a value of 10, 2nd degree a value of 100 and 3rd degree one of 1000 and the severity calculated as the product of Degree Burn× Percentage of Skin Surface Burned. Calculation of COI may also be based on financial impacts, such as treatment and hospitalization costs and lost wages. As an option, a Global COI may be computed by adding to these factors, those related to type, severity or extent of adverse events (e.g. injuries, etc.).

COI associated with degree of injury risk, may be calculated separately from that of injuries. In some embodiments, this may be done by measuring, for example, the percent change in seizure frequency as a function of seizure class. Convulsions and complex partial seizures carry the highest risk of injury, while simple partial seizures (during which awareness is preserved), the lowest. Changes in the degree of injury risk may thus be computed as the decrease in the frequency of a certain seizure class or in their severity. As shown in the example above, this allows distinction between injuries and risk of injuries: COI was halved but the risk of injury was not abolished until detection parameter S4 was programmed.

Adverse Effect rate/unit time and/or Adverse Effect Severity/unit time can be useful metrics. Adverse Effects deal not only with those adverse effects associated with the therapy (including but not limited to seizure aggravation) but also with injuries and embarrassment to patients resulting from false negative detections (or even true detections), response windows with insufficient length (due for example to slow SSzD) to implement safety measures and therapy failure due to late delivery or lack of action. Adverse effect rate denotes the number of adverse effects/unit time. Adverse effect severity may be expressed qualitatively (e.g., Mild, Moderate, Severe) or quantitatively using numerical values (e.g., a fall to the ground without injury=100, a fall to the ground resulting in a concussion=500, a fall to the ground causing head trauma and subdural hematoma=2500, etc.).

Another metric, patient safety, is defined in some embodiments as the decrease in the number of injuries/unit time and in their severity. Since injuries in the case of epilepsy are the results of falls (with or without loss of consciousness) or of transient unawareness and inability to process any cues, preventing falls or unawareness and/or issuing warnings in sufficient time for the patient or caregivers to implement safety measures will translate into decreases in safety risks, a clinically valuable outcome. Decreases in Safety Risks may be calculated as the decrease in the number of seizures/unit time causing falls or unawareness. CoEI calculated as a function of therapeutic efficacy, decreases in injury or in safety risks, is of great medical and practical value and will be addressed in detail below.

Other metrics include, but are not limited to:

Efficacy of Stimulation as a function of Total Electrical Energy/unit time delivered to target (TEEDt): Percentage Seizure Frequency reduction/TEEDt; (TEEDt=[(volts or amps)$^2$×pulse width (in msec)×frequency (in Hz)]/impedance in ohms). Changes in seizure severity may be also used for calculation of this metric. The higher the ratio, the more efficacious the therapy. This concept is also applicable to thermal energy or to drugs.

Wasted Battery Output: Incidents that may waste battery output include but are not limited to: i) false positive detections and the associated stimulations and warnings (in mA); ii) Therapy delivery that does not reduce SzS by a certain percentage or quantity; and iii) Therapy delivery that causes adverse effects. According to various embodiments, waster battery output is a metric of the efficiency of the various functions and, by extension, of the system, and it may be used for optimization.

Although battery life is the least impactful and easier to manage of the various factors that govern the trade-off between sensitivity and specificity of event detection due to the continuous improvements in battery life longevity, including the advent of in-situ rechargeability, it is nonetheless worthy of consideration given that sub-clinical seizure detections (i.e., those associated with changes in biological signals caused by paroxysmal cortical activity whose intensity, duration or extent of spread are not sufficient to cause symptoms, going unrecognized by patients and observers) outnumber, by a considerable margin, clinical seizures which have the highest morbidity and mortality potential.

Time Spent in Detection (TSD) and/or Warning (TSW) and/or Treatment (TST): This refers to the fraction of time per time period (e.g. day, week, month, etc.), spent executing these functions; the magnitude of each of these metrics must be assessed in the context of other costs such as Cost of Treatment, since in isolation they are not highly informative. The TSD, TSW, and/or TST may be optimized individually or collectively. For example, TSW may be reduced without altering TSD or TST, in cases in which warnings caused by false positive detections are affecting quality of life, but stimulation does not cause adverse effects and is efficacious. This approach will improve quality of life and preserve therapeutic efficacy. According to one embodiment, this may be accomplished by setting a higher threshold for issuing warnings than for delivering therapy, meaning there may be instances where the detection of an abnormal biological event would result in the patient receiving a treatment or a therapy, but not receiving a warning from the medical device. Conversely, TST may be shortened by increasing the threshold at which it is delivered, if the therapy is causing adverse effects yet warnings remain beneficial to the patient. This strategy may improve the patient's quality of life without increasing the potential for compromising patient safety.

Warning Efficiency: This is a measure of the system's efficiency in using the warning functionality. According to various embodiments, warning efficiency may be estimated by computing the product of false warnings (FW) per unit time and battery energy spent (in mA): [FW/t×mA]. The higher this metric, the lower the efficiency.

Seizure burden per time t (SBt): This metric or index measures not only seizure frequency and severity, but also reflects the impact of seizures on the patient's health and quality of life. According to various embodiments, SBt is the product of seizure frequency (Fs) and severity (S), divided by the product of quality of life (QOL) scores (e.g. quantitative instrument scores, qualitative scoring, etc.) and the composite score of health status (HS): (Fs×S)/(QOL×HS). This formula takes into account that for certain QOL and HS scores, the larger the number the better the patients' situation, would be changed if the larger score numbers are indicative of a negative outcome.

Optimization efficiency (€): According to various embodiments, this metric may be represented as the number of parameter changes in one set (S) of parameters required to obtain a Pareto-optimal solution. Since the parameters in the contemplated system and method may comprise detection (D) and therapy parameters (T), € may be calculated for both. For example, in one embodiment where the treatment makes use of electrical currents, the parameter set may comprise frequency (in Hz), intensity (in mA or mV), duration (in sec.), pulse waveform (e.g., square) and degree of charge (+ or −) balancing in an electrical pulse. €OP (optimization efficiency with respect to parameters) may be calculated as the number of parameters changed/total number of parameters available for change. As a specific, non-limiting example using electrical stimulation for treatment, if a change in only 1 parameter (e.g., intensity) leads to a Pareto-optimal solution, €OP=⅕=0.2. If changes in intensity and frequency are necessary to obtain a solution, €OP=⅖=0.4. As calculated herein, the lower the ratio value, the higher €OP. These parameters may comprise detection parameters as well as treatment parameters In some embodiments, optimization efficiency (€OP) may also be extended to therapeutic modalities (€OT). In the case of seizures, the therapy modalities include, but are not limited to, electrical currents, pharmacologic or chemical compounds, thermal energy (e.g., tissue cooling or heating), ultrasound, and phototherapy. It should be noted that while the following discussion is focused on these modalities, optimization efficiency in the context of therapy modality may be applied to any present or future treatment.

According to various embodiments, optimization efficiency based on therapeutic modality may be calculated as the ratio of number of treatments required to obtain a Pareto-optimal solution divided by the number of available treatment modalities. As a specific, non-limiting example, if a Pareto-optimal solution is achieved with 1 therapeutic modality (e.g., drugs), and there are 5 available modalities, €OP=⅕=0.2. As calculated herein, the lower the ratio value the higher €OT. In some embodiments, a global optimization efficiency may also be calculated, defined as €OP+€OT.

Efficiency of Adaptation (€A): Generally, accuracy and speed of event detection varies as a function of the architecture of the algorithm applied to the data of interest, and more specifically as a function of certain components or characteristics of the algorithm. To bring this into focus, automated detection of seizures will be used as a non-limiting example. Sensitivity, specificity of detection and the speed at which a detection is issued depend on, among other parameters, the spectral power of the filter(s) applied to the signal and the magnitude of the change in the power of the signal at a certain frequency/frequencies, at which a detection is issued. In turn, these parameters impact the rate of false positive detections and false negative detections. For details about algorithm architecture and parameter adaptation for optimization of seizure detection, the following references are herein incorporated: Osorio I, Frei M G, Wilkinson S B. Real-time automated detection and quantitative analysis of seizures and short-term prediction of clinical onset: Epilepsia 1998 June; 39(6):615-27; Osorio I, Frei M G, Giftakis J, Peters T, Ingram J, Turnbull M, Herzog M, Rise M T, Schaffner S, Wennberg R A, Walczak T S, Risinger M W, Ajmone-Marsan C. Performance reassessment of a real-time seizure-detection algorithm on long ECoG series. Epilepsia 2002 December; 43(12):1522-35; Haas S M, Frei M G, Osorio I. Strategies for adapting automated seizure detection algorithms. Med Eng Phys. 2007 October; 29(8):895-909; Bhavaraju N C, Frei M G, Osorio I. Analog seizure detection and performance evaluation. IEEE Trans Biomed Eng. 2006 February; 53(2):238-45; Osorio I. Automated seizure detection using EKG. Int J Neural Syst. 2014 March; 24(2):1450001.

As previously discussed, the contemplated system and method finds Pareto-optimal "solutions" that are optimal in the context of competing needs of a patient represented by one or more metrics. These solutions are in fact sets of parameters that are modified during the process of finding one or more Pareto-optimal configurations.

According to various embodiments, the set of parameters may comprise detection parameters (e.g. what constitutes an event, etc.), therapy parameters (e.g. variations in how a particular therapy is provided, etc.), and therapy modalities (e.g. the type or types of therapy being administered to the patient in response to the detection of an abnormal biological event, etc.). Each will be discussed, in turn.

According to various embodiments, detection parameters may include, but are not limited to, spectral filter settings, order statistic filter settings, the threshold value for one or more biological signals and/or metrics at which an abnormal biological event is deemed to have been detected, seizure detection algorithm architectures, and the like.

Likewise, according to various embodiments, therapy parameters may include, but are not limited to, a type of therapy within a particular modality, dose, rate of delivery, current intensity, current frequency, current type, current polarity, current waveform, duration of delivery, timing of delivering in relation to time of detection of abnormal event onset, the number of delivery sites, location of delivery sites, and the like.

While therapy modalities could be considered a type of therapy parameter, their impact on the performance or cost of a particular approach to detection, warning, and abatement of abnormal biological events caused by a medical condition can be drastic enough that they warrant being treated separately, according to various embodiments. Therapeutic efficacy of any modality is governed by, among other factors, diffusivity velocity factors. For example, electrical currents diffuse fast into the neuropil, while thermal energy and drugs diffuse slowly. According to various embodiments, a Pareto-optimal solution for drugs or thermal energy would require the fastest possible detection speeds in order to allow the agent to diffuse within the target in time to abate the incipient seizure. According to various embodiments, exemplary therapy modalities include, but are not limited to, a pharmacologic treatment, a thermal treatment, an electrical stimulation, and a cognitive modality.

Pharmacologic and electrical are the modalities most commonly used for the treatment of epileptic seizures. Among anti-seizure therapies delivered directly to brain tissue, electrical stimulation has the fastest diffusion rate, which results in the shortest latency to onset of effects, particularly when compared to pharmacologic or thermal therapies that diffuse slowly, taking tens of seconds to engulf the intended target (e.g., epileptogenic zone in the case of seizures, etc.). As a specific example, seizure control requires that the therapeutic agent promptly reaches the epileptogenic tissue and diffuses throughout it rapidly. In order to compensate for the slow diffusion of drugs and/or thermal energy through brain tissue, SSzD would need to be much faster than would be required for the delivery of electrical therapies, so as to achieve similar efficacy.

In some embodiments, a set of parameters may also include warning parameters. As discussed above, aspects of how and when a warning is delivered, and to whom it is delivered, can have an impact on the patient's quality of life. Exemplary warning parameters include, but are not limited to, type of warning, warning sound, warning volume, warning brightness, warning target, threshold for determining when a warning should be provided, and the like.

As the system and method contemplated herein is used to find one or more Pareto-optimal sets of parameters to be used in the detection, warning, and abatement of abnormal biological events, the set of parameters, which may be a subset of the collection of available parameters, is modified until an acceptability criteria has been satisfied by the CoEI, however it may be defined in that particular implementation. Those parameter modifications, and in some embodiments the acceptability criteria itself, are guided by one or more methods or techniques of optimization.

According to various embodiments, such methods and technique may include, but are not limited to, receiver operating characteristic (ROC) curves, detection error tradeoff (DET) graphs, total operating characteristics (TOC), genetic algorithms, swarm searches, and the like. Those skilled in the art will recognize that other methods and techniques may also be applied to the task of finding a Pareto-optimal set of parameters.

Receiver operating characteristic (ROC) curves are plots of True Positive Detection against the False Positive Rate. An alternative to the ROC curve is the Detection Error Tradeoff (DET) graph, which plots the false negative rate (missed detections) against the false positive rate (false alarms) on non-linearly transformed x- and y-axes. The Total Operating Characteristic (TOC) may be used in addition to or instead of ROC which characterizes diagnostic ability while revealing more information than the ROC. TOC also provides the popular area under the curve of the ROC. A three-dimensional ROC that adds diagnostic latency of detection, the equivalent of speed of detection, to the two-dimensional ROC, may be applied to the CoEI/COD calculation. A reference describing its implementation is incorporated herein (Simon, 2010). Teachings about applying multi-dimensional ROC, to multi-dimensional problems such as optimization of event detection, warning and efficacy of treatment are also incorporated herein (Ferri-Ramirez et al., 2002).

Other methods such as areas under the curve, genetic algorithms and swarm search may be used to optimize CoEI within a multi-dimensional solution space. Regarding speed of event detection, mentioned above in the context of 3D-ROCs, it plays an important role in efficacy of therapy and minimization of injury risks, since the shorter the latency between the appearance of the first signal change indicative of a pathological event and delivery of therapy and issuance of warnings, the higher the probability of blockage or abatement of said events and the lower the number and seriousness of injuries.

It should be noted that many of these methods require, at a minimum, data to be collected round-the-clock for several days, particularly when changes in health or physical fitness occur or when treatments with drugs with autonomic nervous system actions are prescribed. While implantable devices with large data management capabilities may be designed and built, the use of non-implantable, portable devices is preferable for practical and financial reasons.

As mentioned above, the method of optimization may guide which parameters are modified while moving through the solution space. In some embodiments, the method of optimization may also dictate how the CoEI is defined. Similar to the declining temperature used in simulated annealing optimization, which gradually constraints movement within the solution space as the optimization proceeds in an effort to find local minima, some methods may gradually change the definition of CoEI as the optimization proceeds.

As mentioned above, the iterative modification of parameters, the gathering of data and detecting of abnormal biological events, and the evaluation of the CoEI at the end of a time window continues until an acceptability criteria has been met. In the context of the present description and the claims that follow, an acceptance criteria is one or more conditions that must be satisfied in order for a solution (e.g. a set of parameters) to be deemed Pareto-optimal. In some embodiments, the acceptability criteria may be as simple as a CoEI range; solutions having a CoEI within that range are Pareto-optimal. The values of that range will vary widely depending on how CoEI is defined for that particular patient, as goals and priorities may vary from patient to patient. In other embodiments, the acceptability criteria may be more complex. For example, in one embodiment, the acceptability criteria may comprise a logic tree of branching evaluations, each limb comprising a condition that must be met.

The parameter sets associated the costs and metrics discussed above may be deemed as acceptable (i.e. adoptable) or objectionable (i.e. non-adoptable) in a Pareto-optimal sense, based on qualitative and/or quantitative assessments. Quantitative assessments may be based on numerical comparisons among ideal values or historical values.

In some embodiments, the acceptability criteria may comprise a mechanism for terminating an optimization in the face of diminishing returns. For example, in one embodiment, after a predefined number of iterations have elapsed without an improvement in the CoEI, the acceptability criteria may reclassify the best of the previously rejected solutions to now be considered acceptable. Such a situation may be thought of the scenario where an exploration of the solution space has resulted in settling into a local minima (or maxima, depending on how CoEI is defined) that does not satisfy the acceptability criteria, but also from which the search endeavor is unlikely to escape.

As a specific, non-limiting example, the Cost of Event Intervention based on parameters controlling detection performance and speed may be the Cost of Detection (COD), and defined as the reduction in seizure frequency/unit time, plus the number of parameters changed (Seizure frequency+Number of Parameter changes) to achieve a desired solution, a solution which may or may not be acceptable depending on its value and on the total number of searches previously performed and the gains made through those searches; for example if after a certain number of searches, the unacceptable COD yielded by a solution cannot be improved, said solution becomes acceptable. A parameter set contains detection parameters such as spectral filter settings, order statistic filter settings (e.g., median), the threshold value at which a detection is issued, etc. By way of an example (non-limiting) a patient having a mean of 5 seizures/week (3 complex partial and 2 secondarily generalized (convulsions) is implanted with a device for automated detection, quantification, delivery of therapy and warning that is programmed with a first set (S) of detection parameters S1. One month after implantation mean seizure frequency is 4.4/week. In one embodiment, the reference value against which COD is measured is 0 seizures/unit time, or, 100% reduction in seizure frequency/unit time. The COD may be partial if only seizure frequency is taken into consideration, or total if the number of parameters changes made is included. The partial COD based on change in seizure frequency in this patient is: $CODp=(5-0.6)=4.4$ seizures/week or 91% residual frequency, and the total $CODt=4.4+0=4.4$ (the 0 reflects that no detection parameter was changed). In view of COD remaining high, the device is reprogrammed with a second set of parameters S2 in which 2 parameters (detection threshold value & filter power spectral density) are adapted; 1 month later mean seizure frequency is 3/week; $CODp=3$ or 60% residual frequency, $CODt=3+2=5$ Since COD with S2 is still high, a third reprogramming S3 is undertaken (a change in detection threshold value). After 1 month with parameter set S3, mean seizure frequency/week is 1, $CODp=1$ or 20% residual seizure frequency and $CODt=1+1=2$. Additional changes to detection parameters failed to further reduced COD, leading to the discontinuation of this form of uni-dimensional (i.e., using detection parameters only) Pareto-sense optimization. Further improvements (i.e., reduction) in COD could have been attempted and achieved in this example by optimizing, let us say, treatment parameters. Improvements in the treatment of pathologic events may have been achieved not only through optimization of electrical treatment parameters such as intensity, frequency and duration of stimulation, electrical current waveform and/or degree of pulse charge balancing or unbalancing (Direct Current at one end and Alternating Current at the other) but also by employing different therapeutic modalities such as pharmacologic, thermal or cognitive and by changing certain parameters such as drug type, dose, etc. or in the case of thermal, selection of temperature settings and duration.

In another non-limiting example, the optimization of detection parameters is quantitative and the patient's subjective assessment may or may be not requested or taken into consideration. For example, to determine if in a given patient, the results (e.g., seizure frequency, severity, inter-seizure interval, number of false positive detections, number, type and severity of seizure-related injuries or disability, etc.) of automated delivery of a therapy n seconds after detection of a seizure, constitute a Pareto-optimal solution, the timing of therapy delivery in relation to the detection time, may be increased or decreased in relation to n (n1<n>n2), by changing one or more detection parameters, and the therapy results may be compared to those obtained when the latency between detection and therapy delivery was n. This adjustment in speed of detection (upwardly or downwardly) will impact not only sensitivity and specificity rates but also the time available to implement therapeutic and safety measures and adverse effects which encompass those caused by the therapy and delays in warnings (increases risk of injury) or excessive or untimely warnings (increases in distress due to increases in false alarms). Speed of detection, defined as the time (in seconds) elapsed between the first signal change determined using a gold standard such as expert visual analysis and the time an algorithm detects said change (e.g., 5.2 sec. for one set of parameters vs. 2.1 sec. for a different set vs. 0 sec for an ideal detection method; the shorter the time, the faster the speed), false positive and false negative detection as number/unit time (e.g., 1 FP/hour and 1 FN/48 hr.); therapeutic efficacy may be expressed for example, as the percentage change in seizure frequency and/or in severity compared to a reference value. To further the insight into the teachings in this specification another example is provided: A certain change in detection parameters resulted in a prolongation by 2 sec. of the window within which safety and/or therapeutic measures may be implemented which resulted in a decrease in falls to the ground from 3 to 1/month while also decreasing seizure frequency by 20%/unit time and severity by 52%, but increasing the rate of false positive detections from 1/hr. to 2.2/hour. Despite the increase in FP detections, this solution is considered Pareto-optimal as it decreased by a factor of 3 the falls to the ground (which have the potential to cause serious, even fatal injuries) while also decreasing seizure frequency and severity. More specifically, a Pareto-optimal solution in this invention is one which: a) abates or eliminates the most harmful manifestation; or, b) suppresses or lessens the negative impact of a large number of manifestations; or, c) results in the largest improvement in quality of life.

Figure 1:
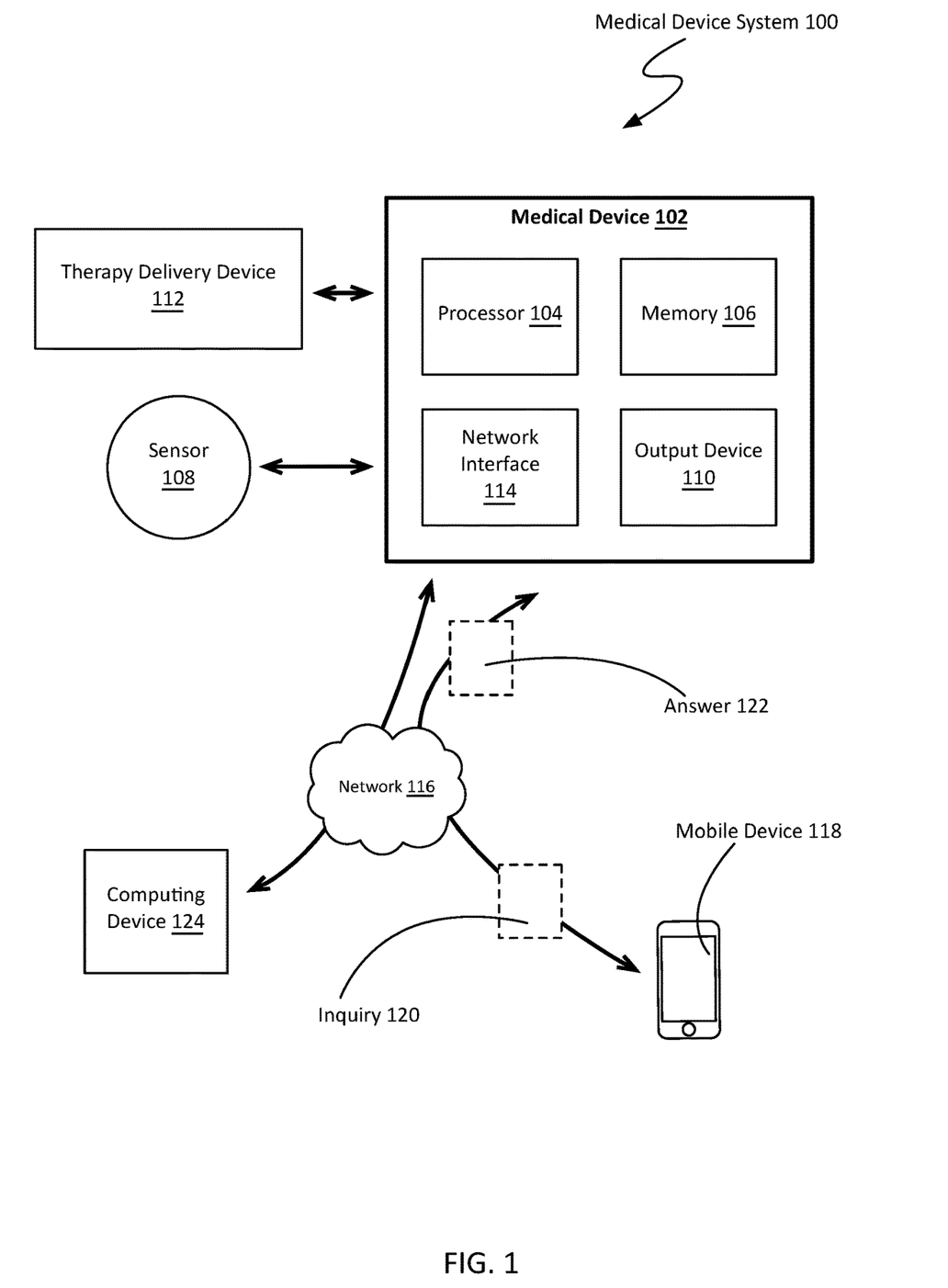
FIG. 1 is a schematic view of a medical device system for the Pareto-optimal automated detection, warning, and abatement of a medical condition.

FIG. 1 is a schematic view of a non-limiting example of a medical device system 100 for finding a Pareto-optimal set of parameters for the detection, warning, and abatement of an abnormal biological event caused by a medical condition, and for performing the detection, warning, and abatement of said events. As shown, the system 100 comprises a medical device 102 communicatively coupled to a sensor 108 and a therapy delivery device 112. Each will be discussed, below.

As shown, the medical device 102 comprises a processor 104 (e.g. general purpose processor, microcontroller, etc.), a memory 106, and an output device 110. In some embodiments, the medical device 102 may also comprise a network interface 114 for communicating with other devices, as will be discussed further, below.

According to various embodiments, the output device 110 is a device configured to communicate with humans (as opposed to a network interface 114, which is configured to communicate with another device). The output device 110 is used to provide a warning to the patient or another interested party, such as a doctor. The warning may be provided in a number of formats, according to various embodiments. Examples of an output device 110 include, but are not limited to, a speaker, a screen, a buzzer, a light, a text-to-speech module (e.g. bespoke warnings may be provided verbally). In some embodiments, the output device 110 is used to provide a warning to the patient or other party of the detection of an abnormal biological event. In other embodiments, such a warning may be provided through another piece of technology that has received instructions regarding the warning from the medical device 102 via a network interface 114 or some other means known in the art. As a specific example, in one embodiment, a warning may be delivered to a patient via their mobile device 118.

According to various embodiments, the medical device 102 is communicatively coupled, either wirelessly or wired, with one or more sensors 108 configured to collect the biological signals discussed above. The sensor 108 of FIG. 1 may represent a single sensor or a plurality of sensors capable of detecting various physiological signals. These one or more sensors 108 are configured to directly capture data of interest from the patient 202.

In the context of the present description and the claims that follow, a therapy delivery device 112 is a device that has been configured to administer some form of therapy (e.g. electrical, pharmaceutical, social, physical, etc.) automatically, based on the senor data available.

In some embodiments, the medical device 102 may further comprise a network interface 114, allowing it to communicate with other devices. As shown in the non-limiting example of FIG. 1, the medical device 102 may be communicatively coupled, via the network interface 114, to a mobile device 118 associated with the patient and/or an external computing device 124. According to various embodiments, the medical device system 100 may make use of external devices for communication, monitoring, and optimizing. For example, as discussed above, in some embodiments the medical device 100 is able to obtain information about at patient's subjective measure of their quality of life. The medical device 102 sends an inquiry 120 that is presented to a patient. The patient responds with and answer 122.

Figure 2A:
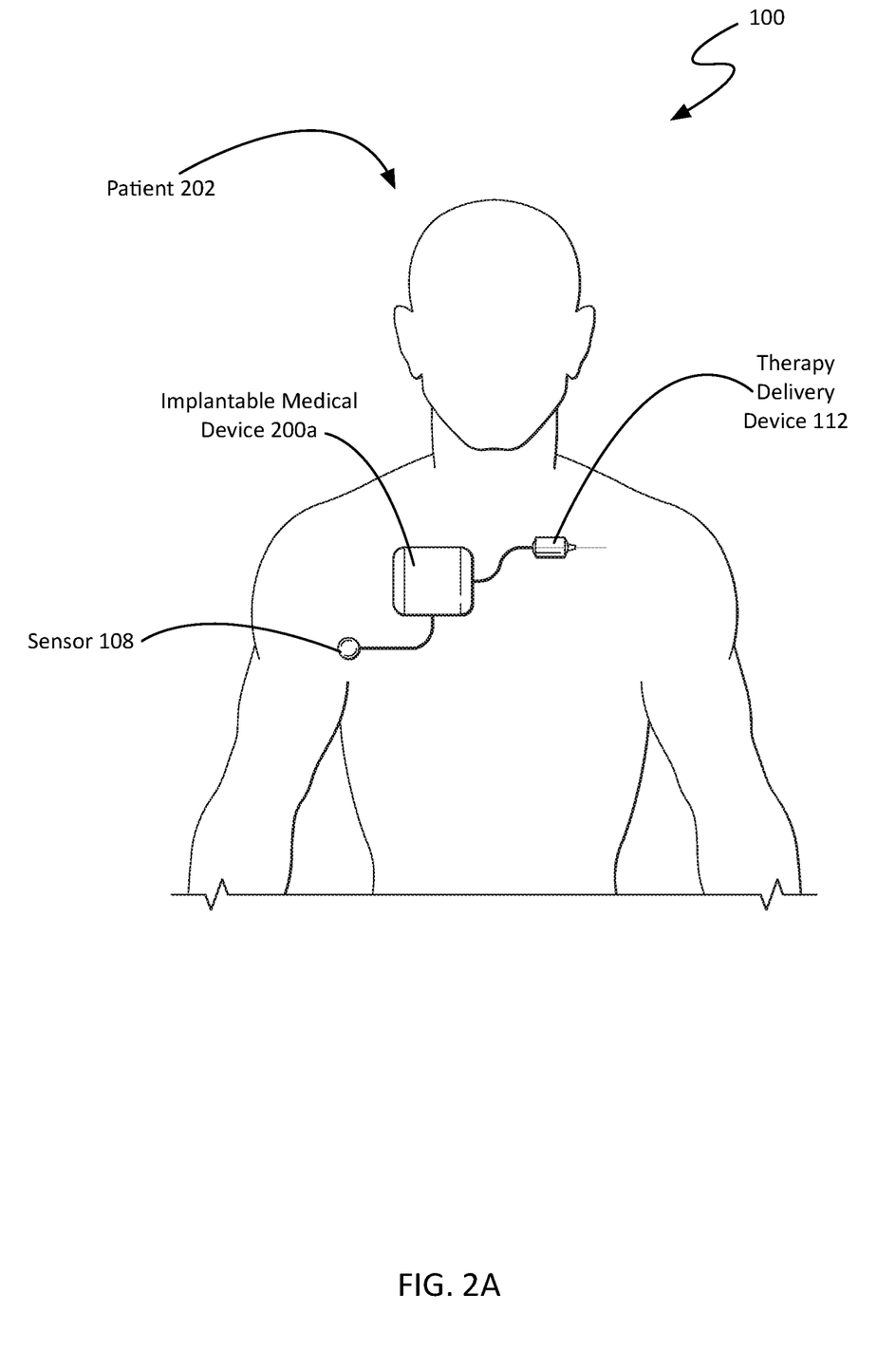
FIGS. 2A and 2B are representative views of medical devices that are implantable and non-implantable, respectively.
Figure 2B:
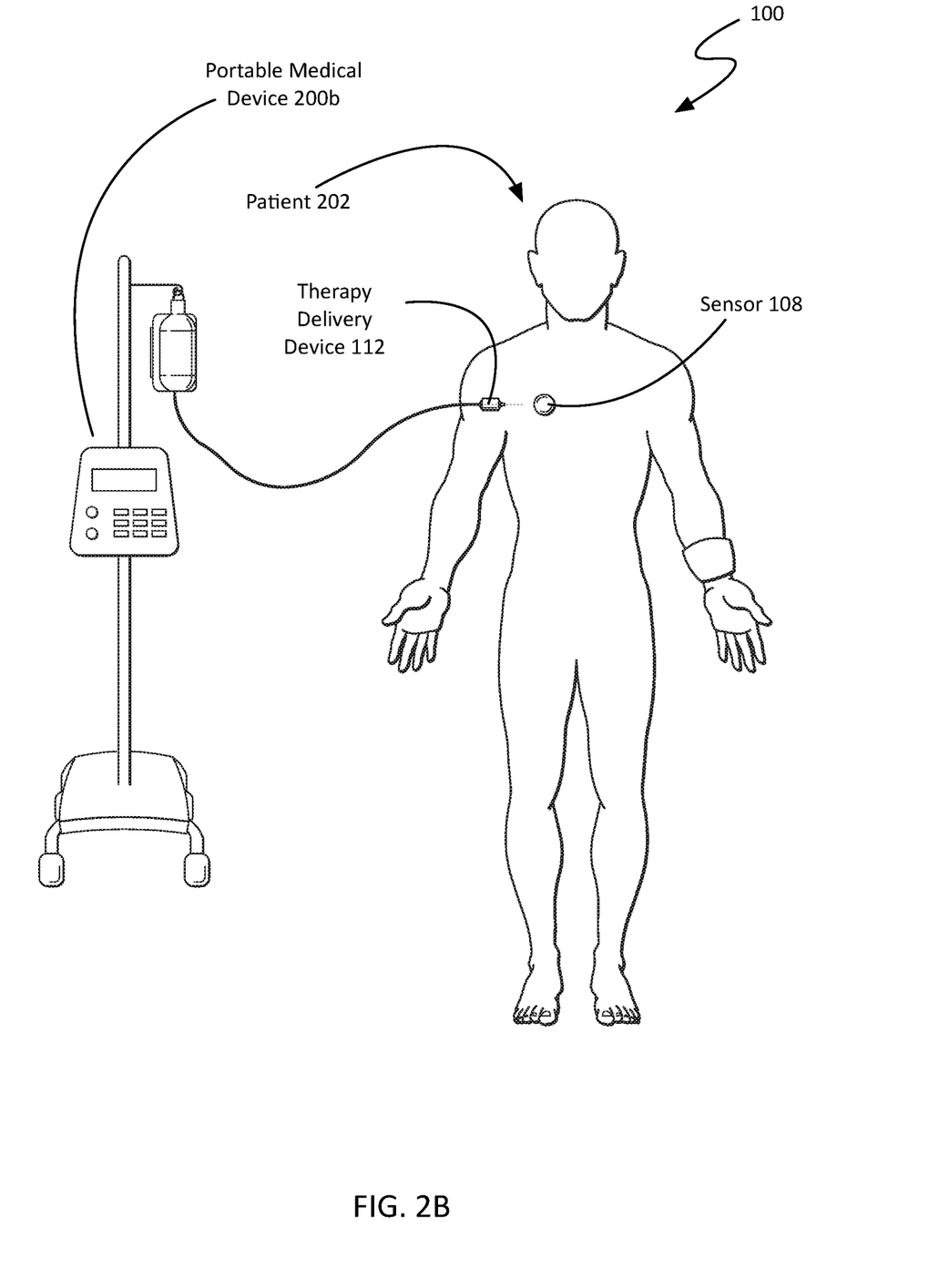

FIGS. 2A and 2B are stylized representations of different embodiments of the medical device system 100 of FIG. 1, deployed for use with a patient 202. Specifically, FIG. 2A shows a non-limiting example of an embodiment of the medical device 102 that is an implantable device 200a, and FIG. 2B shows a non-limiting example of an embodiment of the medical device 102 that is a portable, non-implantable device 200b. The system and method contemplated herein may be implemented in either implanted or portable formats, according to various embodiments. Each hardware environment has benefits and costs. The implantable device 200s is advantageous over portable devices as it presents less of a disruption of a patient's 202 day to day routine. Additionally, it may be used to continually gather data for use in finding a Pareto-optimal solution, as discussed above. Less disruption often means greater patient compliance with whatever protocol has been put into place. Furthermore, the implantable medical device 200*a* is able to capture data using the sensor 108 continuously, while the portable embodiment 200*b* may be temporarily abandoned in circumstances where it would be difficult or inconvenient to transport.

On the other hand, the portable, non-implantable embodiment 200*b* is advantageous over the implantable embodiment 200*a* for a number of reasons. The portable device 200*b* may be plugged into a continuous power source, eliminating any concerns over the energy capacity of a battery. Furthermore, embodiments of the portable device 200*b* are often easier and/or less expensive to implement.

Where the above examples, embodiments and implementations reference examples, it should be understood by those of ordinary skill in the art that other sensors, therapies, medical conditions, and biological events could be intermixed or substituted with those provided. In places where the description above refers to particular embodiments of a system and method for finding a Pareto-optimal set of parameters for the automated detection, warning, and abatement of a medical condition, it should be readily apparent that a number of modifications may be made without departing from the spirit thereof and that these embodiments and implementations may be applied to other detection, warning, and/or abatement system and methods as well. Accordingly, the disclosed subject matter is intended to embrace all such alterations, modifications and variations that fall within the spirit and scope of the disclosure and the knowledge of one of ordinary skill in the art.

REFERENCES

Rosenthal R E. Concepts, Theory, and Techniques PRINCIPLES OF MULTIOBJECTIVE OPTIMIZATION. Decision Sciences 1985; 16:133-52

Goldberg D E. Genetic Algorithms in Search, Optimization, and Machine Learning. Addison-Wesley, Reading, Massachusetts, 1989.

Fonseca C M, Fleming P J. Genetic Algorithms for Multi-objective Optimization: Formulation, Discussion and Generalization. In, Genetic Algorithms: Proceedings of the Fifth International Conference (S. Forrest, ed.), San Mateo, CA: Morgan Kaufmann, July 1993. Fonseca C M, Fleming P J. An overview of evolutionary algorithms in multiobjective optimization. Evolutionary Computation, 3(1):1-16, 1995.

Rendon M V, Uresti-Charre E. A non-generational genetic algorithm for multiobjective optimization. In Proceedings of the Seventh International Conference on Genetic Algorithms, pages 658-665, San Francisco, CA, 1997. Morgan Kaufmann Zitzler E, Thiele L. Multiobjective optimization using evolutionary algorithms—A comparative case study. Parallel Problem Solving from Nature. 5th International Conference Amsterdam, The Netherlands Sep. 27-30, 1998.

Eddy J, Lewis K E. VISUALIZATION OF MULTIDIMENSIONAL DESIGN AND OPTIMIZATION DATA USING CLOUD VISUALIZATION. Proceedings of DETC'02 ASME 2002 Design Engineering Technical Conferences and Computers and Information in Engineering Conference Montreal, Canada, Sep. 29-Oct. 2, 2002; DETC2002/DAC-34130

Ngatchou P, Zarei A, El-Sharkawi A. Pareto Multi Objective Optimization. Proceedings of the 13th International Conference on, Intelligent Systems Application to Power Systems. November 2005; DOI: 10.1109/ISAP.2005.1599245

Kennedy J, Eberhart R. Particle swarm optimization. Proc. IEEE Int. Conf. Neural Netw. 1995; 4: 1942-48.

Eberhart R, Kennedy J. A new optimizer using particle swarm theory. Proc. 6th Int. Symp. Micro Machine and Human Science; 1995: 39-43.

Eberhart R, Shi Y, Kennedy J. Swarm Intelligence. San Mateo, CA: Morgan Kaufmann, 2001

Simon D L. A Three-Dimensional Receiver Operator Characteristic Surface Diagnostic Metric Annual Conference of the Prognostics and Health Management Society, 2010 (NASA Glenn Research Center, Cleveland, OH, 44135; email: Donald.L.Simon@nasa.gov)

Ferri-Ramírez C1, Flach P2, Hernández-Orallol. Multi-dimensional ROC Analysis with Decision Trees. Technical Report 17 Jan. 2002. 1Dep. Sistemes Informàtics i Computació, Univ. Politècnica de València (Spain) {cferri, jorallo}@dsic.upv.es}; 2Department of Computer Science, University of Bristol (United Kingdom) peter.flach@bristol.ac.uk

What is claimed is:

1. A method for finding a Pareto-optimal solution for automated detection, warning, and abatement of a medical condition based on a cost of event intervention in a patient, the method comprising:

acquiring at least one biological signal from the patient via at least one sensor of a medical device, the at least one biological signal comprising at least one of a cardio-vascular signal, a respiratory signal, a dermal signal, an endocrine signal, a metabolic signal, a kinetic signal, and a cerebral signal;

detecting, via the medical device, an abnormal biological event based on changes in the at least one biological signal;

delivering, via the medical device, at least one of a therapy and a warning in response to detection of the abnormal biological event;

logging to a memory a set of parameters applied as part of detecting, warning, and abating the abnormal biological event, the set of parameters comprising at least one of a detection parameter, a therapy parameter, and a therapy modality; and identifying an optimal set of parameters that yield a Pareto-optimal cost of event intervention by iteratively:

collecting and determining at least one metric over a time window, determining the cost of event intervention based on the at least one metric, and modifying at least one parameter of the set of parameters, until the cost of event intervention meets an acceptability criteria, wherein the modifying of the at least one parameter are dictated by one of a receiver operating characteristic curve, a genetic algorithm, and a swarm search.

2. The method of claim 1, wherein the at least one metric is selected from the group consisting of: a time elapsed between onset of the abnormal biological event and the delivery of at least one of the treatment and the warning, a false positive detection rate, a false negative detection rate, an efficacy of the therapy, an adverse event rate, an adverse event type, an adverse event severity, and an adverse event timestamp.

3. The method of claim 1, wherein the at least one metric comprises a qualitative assessment of the quality of life of the patient during the time window, and wherein collecting and determining the qualitative assessment of the quality of life comprises sending an inquiry regarding the quality of life to a mobile device associated with the patient and receiving an answer to the inquiry from the patient via the mobile device.

4. The method of claim 1, wherein the cost of event intervention meets the acceptability criteria when the cost of event intervention is within an acceptable range.

5. The method of claim 1, wherein the detection parameter is at least one of a spectral filter setting, an order statistic filter setting, a detection threshold value beyond which the abnormal biological event is considered detected, and a seizure detection algorithm architecture, and wherein the therapy parameter is at least one of a type of therapy, a dose, a rate of delivery, a current intensity, a current frequency, a current type, a current polarity, a current waveform, a duration of therapy delivery, a timing of delivering therapy with respect to onset of the abnormal biological event, a number of delivery sites, and a delivery site location.

6. The method of claim 1, wherein the cost of event intervention is based on at least one of a cost of detection, a cost of treatment, a cost of injuries, a warning efficiency, an optimization efficiency, an adaptation efficiency, a seizure burden per unit time, an efficacy of electrical stimulation as a function of total electrical energy delivered/unit time, a time spent in detection, a time spent in warning, and a time spent in treatment.

7. A method for finding a Pareto-optimal solution for automated detection, warning, and abatement of a medical condition based on a cost of event intervention in a patient, the method comprising:
acquiring at least one biological signal from the patient via at least one sensor of a medical device, the at least one biological signal comprising at least one of a cardio-vascular signal, a respiratory signal, a dermal signal, an endocrine signal, a metabolic signal, a kinetic signal, and a cerebral signal;
detecting, via the medical device, an abnormal biological event based on changes in the at least one biological signal;
delivering, via the medical device, at least one of a therapy and a warning in response to detection of the abnormal biological event;
logging to a memory a set of parameters applied as part of detecting, warning, and abating the abnormal biological event, the set of parameters comprising at least one of a detection parameter, a therapy parameter, and a therapy modality; and
identifying an optimal set of parameters that yield a Pareto-optimal cost of event intervention by iteratively:
collecting and determining at least one metric over a time window,
determining the cost of event intervention based on the at least one metric, and
modifying at least one parameter of the set of parameters, until the cost of event intervention meets an acceptability criteria, wherein the acceptability criteria is defined using one of a receiver operating characteristic curve, a genetic algorithm, and a swarm search.

8. The method of claim 7, wherein the at least one metric is selected from the group consisting of: a time elapsed between onset of the abnormal biological event and the delivery of at least one of the treatment and the warning, a false positive detection rate, a false negative detection rate, an efficacy of the therapy, an adverse event rate, an adverse event type, an adverse event severity, and an adverse event timestamp.

9. The method of claim 7, wherein the cost of event intervention is based on at least one of a cost of detection, a cost of treatment, a cost of injuries, a warning efficiency, an optimization efficiency, an adaptation efficiency, a seizure burden per unit time, an efficacy of electrical stimulation as a function of total electrical energy delivered/unit time, a time spent in detection, a time spent in warning, and a time spent in treatment.

10. The method of claim 7, wherein the therapy is at least one of a pharmacologic treatment, a thermal treatment, and an electrical stimulation.

11. The method of claim 7, wherein the medical device is one of an implantable device and a portable device outside of the patient.

12. The method of claim 7, wherein the abnormal biological event is a seizure, and the medical condition is at least one of cardiac arrhythmia, fainting, and pain.

13. A medical device system for finding a Pareto-optimal solution for automated detection, warning, and abatement of a medical condition based on a cost of event intervention in a patient, the system comprising:
at least one sensor, a therapy delivery device, and a medical device having an output device, a processor, and a memory, the medical device configured to:
acquire at least one biological signal from a patient using the at least one sensor, the at least one biological signal comprising at least one of a cardio-vascular signal, a respiratory signal, a dermal signal, an endocrine signal, a metabolic signal, a kinetic signal, and a cerebral signal;
detect an abnormal biological event based on changes in the at least one biological signal;
deliver at least one of a therapy using the therapy delivery device and a warning using the output device, in response to detection of the abnormal biological event;
log to a memory a set of parameters applied as part of detecting, warning, and abating the abnormal biological event, the set of parameters comprising at least one of a detection parameter, a therapy parameter, and a therapy modality; and
identify an optimal set of parameters that yield a Pareto-optimal cost of event intervention by iteratively:
collecting and determining at least one metric over a time window,
determining the cost of event intervention based on the at least one metric, and
modifying at least one parameter of the set of parameters, until the cost of event intervention meets an acceptability criteria, wherein the modifying of the at least one parameter is dictated by one of a receiver operating characteristic curve, a genetic algorithm, and a swarm search.

14. The system of claim 13, wherein the medical device is implantable in the patient.

15. The system of claim 13, wherein the medical device is a portable device outside of the patient.

16. The system of claim 13, wherein the abnormal biological event is a seizure, and the medical condition is at least one of cardiac arrhythmia, fainting, and pain.

17. The system of claim 13, wherein the cost of event intervention is based on at least one of a cost of detection, a cost of treatment, a cost of injuries, a warning efficiency, an optimization efficiency, an adaptation efficiency, a seizure burden per unit time, an efficacy of electrical stimulation as a function of total electrical energy delivered/unit time, a time spent in detection, a time spent in warning, and a time spent in treatment.

18. The system of claim 13:
- wherein the medical device is communicatively coupled to a mobile device associated with the patient through a network;
- wherein the at least one metric comprises a qualitative assessment of the quality of life of the patient during the time window; and
- wherein collecting and determining the qualitative assessment of the quality of life comprises sending an inquiry regarding the quality of life to the mobile device and receiving an answer to the inquiry from the patient via the mobile device.

19. The system of claim 13, wherein the at least one metric is selected from the group consisting of: a time elapsed between onset of the abnormal biological event and the delivery of at least one of the treatment and the warning, a false positive detection rate, a false negative detection rate, an efficacy of the therapy, an adverse event rate, an adverse event type, an adverse event severity, and an adverse event timestamp.

20. The system of claim 13, wherein the detection parameter is at least one of a spectral filter setting, an order statistic filter setting, a detection threshold value beyond which the abnormal biological event is considered detected, and a seizure detection algorithm architecture, and wherein the therapy parameter is at least one of a type of therapy, a dose, a rate of delivery, a current intensity, a current frequency, a current type, a current polarity, a current waveform, a duration of therapy delivery, a timing of delivering therapy with respect to onset of the abnormal biological event, a number of delivery sites, and a delivery site location.

* * * * *